Figure 2:
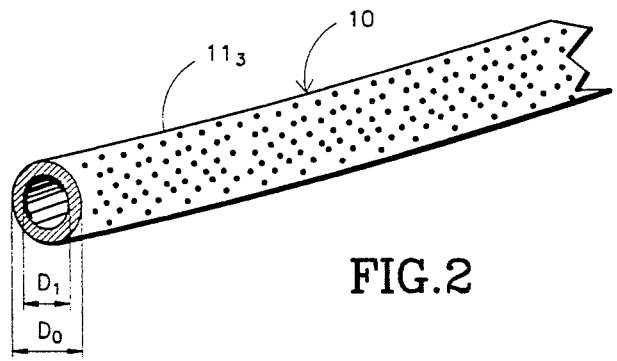

United States Patent [19]
Swan

[11] Patent Number: 5,125,834
[45] Date of Patent: Jun. 30, 1992

[54] APPARATUS, AND METHOD, FOR SIMULTANEOUS FLOSSING AND SUBGINGIVAL INJECTION WITH ANTIBACTERIAL LIQUID SOLUTION TO PREVENT PLAQUE BUILDUP ON TEETH

[76] Inventor: George A. Swan, 18437 Wildlife Way Dr., Baton Rouge, La. 70817

[21] Appl. No.: 734,288

[22] Filed: Jul. 15, 1991

[51] Int. Cl.$^5$ ............................................. A61G 17/02
[52] U.S. Cl. ..................................... 433/80; 433/216; 132/321
[58] Field of Search ....................... 433/80, 87, 88, 89, 433/215, 136, 216; 132/321, 322, 323

[56] References Cited

U.S. PATENT DOCUMENTS 4,175,326  11/1979  Goodson ............................... 433/80
4,776,358  10/1988  Lorch ................................... 132/321

Primary Examiner—Cary E. O'Connor
Attorney, Agent, or Firm—Llewellyn A. Proctor

[57] ABSTRACT

Apparatus, and method, for flossing the teeth, and simultaneously applying an antibacterial liquid solution to the teeth being flossed. The apparatus is constituted generally of a flexible hollow fiber with porous walls of diameter sufficiently small for fitting between and flossing the teeth, and a positive displacement device for supplying an antibacterial liquid to the interior volume, or bore, of the flexible hollow fiber for transport through the porous walls to the teeth. Flossing with the flexible hollow fiber, to which the antibacterial liquid solution is applied during flossing, bathes the teeth with the liquid solution during the flossing and provides a significant reduction in plaque accumulation.

20 Claims, 1 Drawing Sheet ically derived material which is utilized for scraping and polishing the roots of teeth to dislodge and remove accumulations of bacterial plaque. These anaerobic bacteria in a mucuous-like film produce toxic metabloic products which irritate gum tissue and lead to gingivitis. If not promptly treated gingivitis eventually becomes periodontitus which attacks the bone and tooth support structure, ultimately causing loss of teeth. Gingivitis is painless and can go undetected until well advanced, and it is estimated that over half of the adult population in the United States experiences some degree of gingivitis.

APPARATUS, AND METHOD, FOR SIMULTANEOUS FLOSSING AND SUBGINGIVAL INJECTION WITH ANTIBACTERIAL LIQUID SOLUTION TO PREVENT PLAQUE BUILDUP ON TEETH

FIELD OF THE INVENTION

This invention relates to novel apparatus, and method for flossing teeth. In particular, it relates to apparatus and method permitting subgingival injection of antibacterial liquid solutions for enhanced removal and control of bacterial plaque during flossing.

BACKGROUND

Daily flossing is recommended by most dentists to prevent harmful plaque buildup, this resulting from a condition known as gingivitis. Dental floss is a widely used appliance for oral hygiene. It is typically a filament, thread, or strand of synthetic or naturally derived material which is utilized for scraping and polishing the roots of teeth to dislodge and remove accumulations of bacterial plaque. These anaerobic bacteria in a mucuous-like film produce toxic metabloic products which irritate gum tissue and lead to gingivitis. If not promptly treated gingivitis eventually becomes periodontitus which attacks the bone and tooth support structure, ultimately causing loss of teeth. Gingivitis is painless and can go undetected until well advanced, and it is estimated that over half of the adult population in the United States experiences some degree of gingivitis.

Flossing techniques comprise both scraping and polishing actions. With the extremities of the filament held in the hands, the scraping motion involves insertion of the floss between adjacent teeth or behind back teeth, working it beneath the gum line in a partially vertical, partially horizontal motion along the roots of teeth. Polishing action comprised of horizontal or back and forth motion of the floss over the roots of teeth further effects their cleansing of plaque.

Various improvements to dental floss have been made over the years to increase its effectiveness for plaque removal and maintenance of healthy gums; among these are waxing the filaments and altering their geometry from a cylindrically shaped filament to that of a flat ribbon. Fibrous floss or yarn similar to embroidery thread has also proven very effective for scavenging plaque beneath the gums, since it provides significantly greater contact surface area per unit of length than conventional floss. U.S. Pat. No. 4,941,487 discloses a ribbon or string-like floss onto which multiple, discrete segments of a fluoride coating are applied; the benefit is fluoride treatment of teeth concurrently with flossing. U.S. Pat. No. 4,265,258 teaches a larger diameter floss comprised of individual fibers overlaid such that they provide extended cleaning ability via higher surface area and better shock absorbancy. In the same vein U.S. Pat. No. 4,142,538 covers two step preparation of an improved, continuous length tooth cleaner wherein a coated string is subsequently modified by a second coating to impart alternating brush-like segments which aid in flossing.

A related technology is disclosed in U.S. Pat. No. 4,304,245 wherein a therapeutic toothpick is formed via rolling thin sheets of polymeric material into a hollow tube with spiraling ridges and tapered ends. In one embodiment liquids such as medicines, disinfectants, or breath fresheners are placed into the hollow core for supply to the oral cavity or interproximal space. This novel toothpick is claimed to both remove particles from between teeth and massage gingival surfaces, but not penetrate or damage the inner surfaces of the oral cavity. Hence it would not be applied beneath the gum line.

While these and other prior art dental appliances have utility for improving oral hygiene, they nevertheless suffer limitations, principally in that they are limited to mechanical action to remove plaque, particularly from the roots of teeth.

OBJECTS

It is, accordingly, an objective of the present invention to correct this and other prior art deficiencies.

In particular, it is an object to provide apparatus, and process, for removing plaque from the teeth.

A more specific object is to provide an improved dental floss which combines mechanical action and hydraulic action with injection of a suitable antibacterial liquid, notably a liquid oxidizing agent, beneath the gum line to substantially remove plaque deposits and kill the remaining bacteria.

A yet further object is to provide means for the utilization of said floss in combination with ancillary devices for injecting peroxide-containing solutions through the floss either continuously or intermittently during the process of flossing.

THE INVENTION

These objects and others are achieved in accordance with this invention embodying apparatus and method which utilizes porous hollow fibers characterized as small diameter flexible mini-tubes or dental floss with porous walls which permit controlled flow of a liquid peroxidizing antibacterial solution from the interior volume or bore outward to the exterior surface, and means for supplying the liquid to the interior volume of the porous hollow fibers for application to the roots of the teeth. Convenient lengths of the hollow fibers are sealed at one end, while a suitable liquid peroxidizing solution such as aqueous hydrogen peroxide is injected, pumped, or otherwise supplied to the opposite end of the bore, either continuously or intermittently, while the floss is in use. As pressure in the fiber bore is increased, liquid is forced into the interior volume of the porous hollow fibers and through the walls, wetting the exterior surface as the fiber is placed between the teeth and engaged in mechanically cleaning plaque deposits from the teeth. This provides complementary flushing action as the roots of teeth are bathed with the peroxidizing, antibacterial solution. Significant reduction in plaque accumulation results together with healthier gums.

This invention, and its principle of operation, will be more fully understood by reference to the following detailed description of specific and preferred embodiments, and to the attached drawing to which reference is made in the description. In the different views, identical numbers are used to designate corresponding parts, or components.

Figure 1:
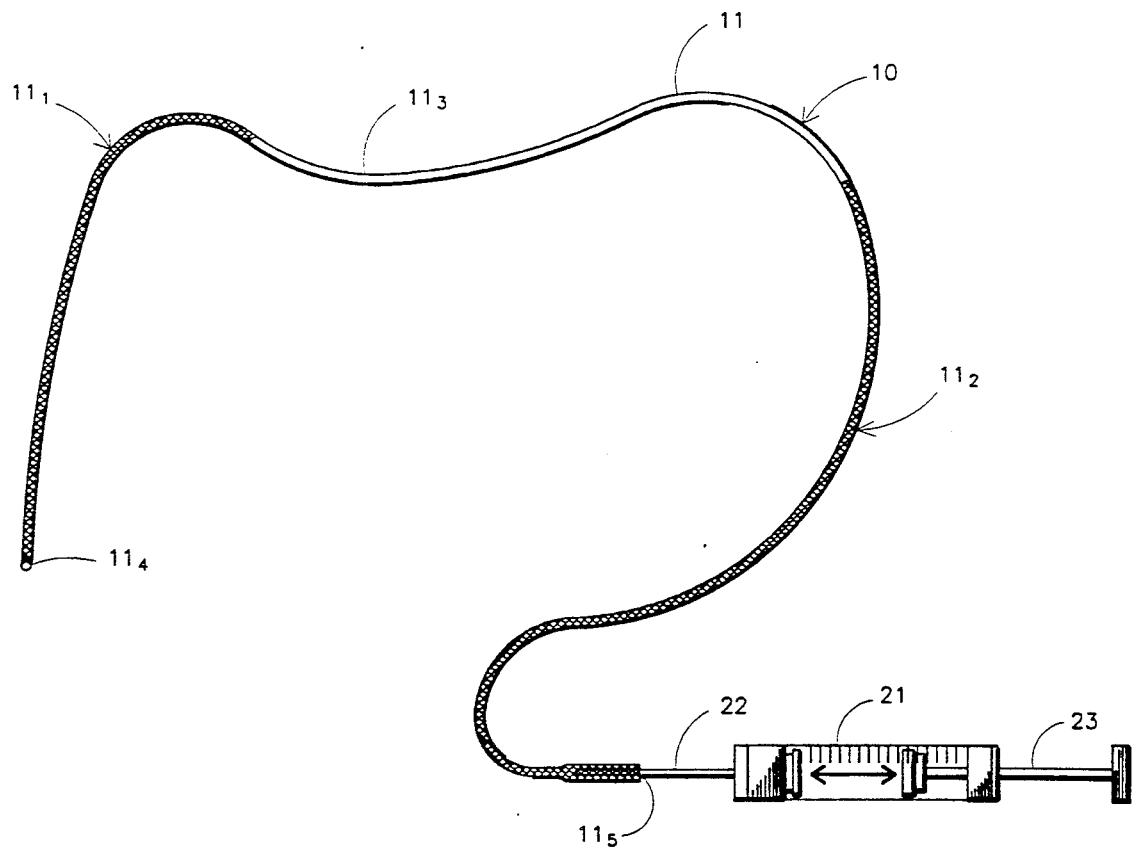

In the drawing:

FIG. 1 depicts apparatus characterized as a working length of a tubular, or hollow fiber floss coated at its extremities with an agent to seal the pores, leaving the center zone micropores available for liquid transfer, one end of the tubular shaped floss being sealed while the other is attached to a suitable liquid injection device for pressurized delivery of an antibacterial liquid solution into the tube for transfer through the micropores for contact with the teeth when the hollow fiber floss is in use.

FIG. 2 depicts an enlarged view a segment of said hollow fiber described with reference to the preceding figure, with Di denoting the inside diameter of the tube and Do referring to the overall or outside diameter of the tube.

Referring to the figures, there is shown generally an apparatus 10 constituted of a hollow tubular fiber 11 with microporous walls, useful in the manner of dental floss, and pumping means 21 for supplying an antibacterial liquid solution under pressure to the tube for transport through the micropores. In particular, referring directly to FIG. 1, a working length of hollow fiber floss 11 is coated at its extremities $11_1$, $11_2$ (shaded regions) with an agent to seal the pores, leaving the center zone $11_3$ micropores available for liquid transfer. The shaded regions $11_1$, $11_2$ are held in the hands external to the mouth, and the center zone $11_3$ is passed between the teeth (not shown). One extremity $11_4$, of the fiber is sealed, or plugged, while the other $11_5$ is connected to a suitable liquid injection device, or pump 21 capable of pressurized delivery of antibacterial solution into the tube and thence through the micropores to contact the roots of teeth when the hollow fiber floss is in use.

Utilization of porous hollow fiber 11 as dental floss facilitates improved oral hygiene via enhanced control and removal of bacterial plaque from the teeth. An antibacterial liquid solution is injected via action of pump 21 concurrently with flossing, thereby effecting both mechanical and hydraulic removal of plaque and chemical or oxidative attack upon the residual bacteria. The liquid antibacterial agent is injected under pressure into an end $11_2$ of the interior volume or bore of the hollow fiber; the liquid being transported through the microporous walls at center section $11_3$ of the hollow fiber into contact with the teeth. Increasing the rate of liquid injection forms microscopic jets of antibacterial solution which provide turbulent, hydraulic cleaning action.

Hollow fibers per se useful in the practice of this invention are well known in the art, and are formed from either natural or synthetic polymers. For example, U.S. Pat. No. 3,876,738 describes a variety of hollow tubes formed via a process for manufacturing porous or microporous membranes from polymeric solutions, especially nylon polymers. Controlled pore size is achieved via controlling aggregation of polymer molecules, and the polymer solution is extruded to produce hollow continuous tubes using a hollow tube die and suitable spinning techniques. Polymer membranes comprised of polypropylene, polysulfone, or polyacrylonitrile can also be formed into hollow fibers with pore size up to about 5 uM (micrometers). By pore size is meant the average dimension of openings in the fiber wall which would exclude a particle of that dimension if the fiber were to be used for microfiltration of particulate solids suspended in a liquid. The preferred pore structure is isotropic with substantially uniform pore size and shape along any cross sectional axis of the fiber wall.

Referring specifically to FIG. 2, the hollow fibers of particular utility for this invention are formed from polymeric solutions such that their overall diameter, Do, is in the range of 100 to 1000 uM, with the ratio of outside diameter, Do, to interior diameter, Di, (Do/Di) ranging from about 1.2 to about 10.0, and preferably from about 1.2 to about 5.0. Adequate wall thickness must be ensured for sufficient tensile strength to prevent failure of the fiber during flossing as it is mechanically stressed. The wall is of thickness (Do−Di)/2, and the wall is characterized by the presence of micropores with average diameter in the range of from about 0.01 uM to about 5 uM, preferably from about 0.01 uM to about 1.0 uM, and more preferably from about 0.01 uM to about 0.5 uM. Typical ratio of working length, $11_3$, of the fiber to outer diameter, Do, is greater than about 100. Hollow fibers satisfying these requirements are readily formed, e.g., from Nylon, such as Nylon 6/6 or, polypropylene. These fibers are particularly advantageous for practicing this invention.

A specific mode of supplying a hollow fiber dental floss with antibacterial solution injection is now described by specific reference to FIG. 1. A convenient length of fiber is utilized wherein one end $11_4$ is sealed and the other connected to a positive displacement type injection mechanism, suitably a pump or syringe. Typically, the syringe 21 is constituted of a tubular barrel, a forwardly projecting nozzle 22 of relatively small diameter and a rearward piston 23, reciprocably mounted within the bore of the barrel for applying a force upon liquid supplied to the barrel. The projecting nozzle 22 is projected into an end $11_5$ of the hollow fiber 11, and affixed therein so that an application of force by the plunger 23 upon a liquid contained within the barrel will force liquid into the hollow fiber 11. A seal $11_5$ such as glue or epoxy is utilized to prevent leakage at this connection. The extremities $11_1$, $11_2$ of the fiber are coated with an agent to seal the micropores in these regions and thereby prevent liquid flow in the hand held area, depicted in this figure as shaded areas. The central region $11_3$ of the fiber wall remains permeable for liquid transfer. A suitable liquid antibacterial solution is charged to the reservoir, or bore of the positive displacement device which is external to the mouth and may be attached to the wrist of an operative for convenience. Operation of the syringe, or positive displacement pump may be automatic as for example an electrically driven pump, or it may be manual.

A precision metering pump such as those manufactured by the Milton Roy Company may be employed for this service. These are positive displacement pumps containing a mechanical drive unit, a reciprocating plunger assembly, and check valves in the liquid end (suction and discharge). These pumps are capable of delivering the requisite liquid injection rates at discharge pressures in excess of 2,000 psig, and thus they are especially suitable for use with hollow fibers whose average micropore diameters are near the low end of the preferred range.

It is understood that a specific liquid injection mechanism is not critical to the practice of this invention, and various pumping devices known to the art may be employed without departing from the spirit or scope of this invention.

A suitable length of "leader" filament may be attached on the sealed fiber end opposite the positive displacement pump to facilitate insertion of the hollow fiber floss between close adjacent teeth. With the fingers of the operative gripping the extremities, the hollow fiber floss is inserted between teeth and under the gum line as the plunger 23 forces antibacterial liquid into the bore of the fiber, thence through the microporous walls to the external surface as the floss is manipulated in a scraping or polishing motion across the roots of teeth. Micro-jets of liquid bathe these roots with the antibacterial solution either continuously or intermittently (pulsed).

A preferred antibacterial solution contains from 1 to 10 weight percent hydrogen peroxide; as it contacts the gum tissue, hydrogen peroxide is decomposed, liberating molecular oxygen which kills the plaque-forming anaerobic bacteria. However, any liquid anti-plaque reagent available on the market may be advantageously employed with the hollow fiber dental floss of this invention. Liquid injection rates range from about 1 to about 100 cc (cubic centimeters) per minute, although typically from about 5 to about 50 cc per minute are adequate. For a hollow fiber with Do=500 uM and a 25 cm (centimeter) active working length, the typical injection rates correspond to 1–15 cc liquid/cm2 contact area (exterior fiber surface area)/minute for continuous liquid injection.

The utility of this invention will be better understood via the following illustrative examples, which serve to demonstrate specific embodiments.

EXAMPLE 1

A 23 cm long hollow fiber made of Nylon 6/6 with overall diameter, Do=1000 uM, and interior diameter, Di=500 uM, and whose microporous walls contain pores in the range of 0.1 to 0.2 uM average diameter was utilized with a syringe as illustrated in FIG. 1. An aqueous solution containing 3.0 weight percent hydrogen peroxide (U.S.P.) was charged to the reservoir of the manually operated syringe. This flossing device was used effectively with intermittent liquid injection (1 cc) to maintain a coating of hydrogen peroxide solution on the external surface of the fiber as it was engaged in dislodging bacterial plaque from the roots of teeth. As the hollow fiber was tensioned in the polishing mode its antibacterial, longitudinal liquid coating rendered it superior to conventional dental floss for improved plaque control. In addition to typical mechanical removal of plaque, the hydraulic action of the hollow fiber floss with subgingival liquid micro-jets (as liquid solution is forced through the micropores) greatly improves the efficiency by which plaque is either removed or ultimately destroyed by the oxidizing power of the residual hydrogen peroxide solution.

EXAMPLE 2

The same Nylon 6/6 hollow fiber floss as used in Example 1 was employed with a mouthrinse solution available commercially under the Peroxyl trademark (U.S. Pat. Nos. 4,431,631 and 4,537,778) containing 1.5 weight percent hydrogen peroxide and 6 weight percent alcohol. The flossing procedure described previously was successfully repeated.

EXAMPLE 3

A microporous hollow fiber manufactured from high purity, food grade polypropylene, characterized by external diameter Do=300 uM and interior diameter, Di=240 uM was selected for testing in accordance with this invention. Its average transwall pore size was 0.03–0.05 uM, and it was utilized with a commercial liquid product marketed under the Listerine trademark and claimed to control plaque. This liquid solution contains 27 volume percent alcohol in addition to the active antibacterial ingredients, the alcohol serving as a wetting agent for the fresh fibers which are normally hydrophobic. A particular advantage of the polypropylene fibers is their elasticity during manipulation under the gum line and in polishing the roots of teeth in the flossing regimen.

EXAMPLE 4

The microporous polypropylene hollow fibers in Example 3 were applied with the 1.5 weight percent hydrogen peroxide solution containing 6 weight percent alcohol described in Example 2, and the above flossing procedure was duplicated. As in the previous example, the apparatus was successful in removing, and controlling plaque.

It is apparent that various modifications can be made without departing the spirit and scope of the invention. Changes may thus be made, e.g., in size, shape, or in the absolute and relative dimensions of the parts, materials used and the like, as well as in the type of positive displacement device used for the injection of antibacterological liquid solution into the hollow fibers.

Having described the invention, what is claimed is:

1. Apparatus for simultaneously flossing and injecting an antibacterial liquid solution upon the roots of the teeth to control, and prevent plaque buildup which comprises the combination of a flexible hollow fiber of continuous length with two unfettered ends formed by a wall surrounding a bore to which said antibacterial liquid solution can be supplied, the wall is characterized by the presence of pores of diameter sufficient for the liquid transfer of said antibacterial liquid solution from the bore to the surface of the fiber, the fiber is sealed at one of its two ends, and said fiber is one having an outside diameter sufficiently small that said fiber can be passed between the teeth and the teeth flossed, and means for supplying under pressure antibacterial liquid solution to the bore from the end opposite the sealed end of the fiber, and transport of the antibacterial liquid solution through the pores in the wall of the fiber to wet the exterior wall surface of the fiber to provide a complementary flushing action and bathe the roots of the teeth as the fiber is pulled back and forth through the teeth during flossing.

2. The apparatus of claim 1 wherein pores within the wall sections at the terminal ends of the fiber are coated with an agent to seal the pores, leaving the central section of the fiber with open wall pores suitable for liquid transfer from the bore to the wall exterior.

3. The apparatus of claim 2 wherein the means for supplying the antibacterial liquid solution to the bore of the fiber is a positive displacement pump.

4. The apparatus of claim 1 wherein the fiber is formed from a polymer selected from the group consisting of natural polymer fibers and synthetic polymer fibers.

5. The apparatus of claim 4 wherein the polymer is selected from the group consisting of Nylon fibers, polypropylene fibers, polysulfone fibers and polyacrylonitrile fibers.

6. The apparatus of claim 1 wherein the pores in the wall of the fiber are of diameter ranging from about 0.01 micrometers to about 5 micrometers.

7. The apparatus of claim 1 wherein the outside diameter of the fiber ranges from about 100 micrometers to about 1000 micrometers, with the ratio of the outside diameter of the fiber to its inside diameter ranging from about 1.2 to about 10.0.

8. The apparatus of claim 7 wherein the ratio of the outside diameter of the fiber to its inside diameter ranges from about 1.2 to about 5.0.

9. An apparatus for simultaneously flossing and injecting an antibacterial liquid solution upon the roots of the teeth of an operative to control, and prevent plaque buildup on the teeth which comprises, in combination,
- a flexible hollow fiber formed by a wall surrounding a bore to which said antibacterial liquid solution can be supplied, the wall is provided with pores, the pores within the wall sections at the terminal ends of the fiber are coated with an agent to seal the pores, the pores within the wall of the central section are open and of diameter ranging from about 0.01 micrometers to about 5.0 micrometers, suitable for liquid transfer from the bore to the exterior wall of the fiber, one terminal end of the fiber is plugged, and
- a positive displacement device connected to, and operatively engaged with the open terminal end of the fiber for supplying antibacterial liquid solution to the bore of the fiber,
- whereby the coated ends of the fiber provide areas for gripping by the hands of the operative, the center section provides a working length for engagement with the teeth and transport of the antibacterial liquid solution to wet the exterior wall surface of the fiber to provide a complementary flushing action and bathe the roots of the teeth during flossing.

10. The apparatus of claim 9 wherein the fiber is formed from a polymer selected from the group consisting of natural polymer fibers and synthetic polymer fibers.

11. The apparatus of claim 10 wherein the polymer is selected from the group consisting of Nylon fibers, polypropylene fibers, polysulfone fibers, and polyacrylonitrile fibers.

12. The apparatus of claim 9 wherein the pores in the wall at the central section of the fiber ranges from about 0.01 micrometers to about 1.0 micrometers.

13. The apparatus of claim 12 wherein the pores range from about 0.01 micrometers to about 0.5 micrometers.

14. The apparatus of claim 12 wherein the ratio of the working length of the fiber to the outer diameter of the fiber is greater than about 100.

15. The apparatus of claim 9 wherein the outside diameter of the fiber ranges from about 100 micrometers to about 1000 micrometers, with the ratio of the outside diameter of the fiber to its inside diameter ranging from about 1.2 to about 10.0.

16. The apparatus of claim 15 wherein the ratio of the outside diameter of the fiber to its inside diameter ranges from about 1.2 to about 5.0.

17. A process for simultaneously flossing and injecting an antibacterial liquid solution upon the roots of the teeth to control, and prevent plaque buildup on the teeth which comprises
- flossing the teeth with a flexible hollow fiber of continuous length with two unfettered ends formed by a wall surrounding a bore to which said antibacterial liquid solution can be supplied, the wall is characterized by the presence of pores of diameter sufficient for the liquid transfer of said antibacterial liquid solution from the bore to the surface of the fiber, and said fiber is one having an outside diameter sufficiently small that said fiber can be passed between the teeth, and
- supplying an antibacterial liquid solution to the bore of the fiber sufficient that said solution is transported through the porous wall of the fiber to wet the exterior wall surface of the fiber to provide a complementary flushing action and bathe the roots of the teeth during flossing.

18. The process of claim 17 wherein the pores in the wall of the fiber are of diameter ranging up to about 5 micrometers.

19. The process of claim 18 wherein the outside diameter of the fiber ranges from about 100 micrometers to about 1000 micrometers, with the ratio of the outside diameter of the fiber to its inside diameter ranging from about 1.2 to about 10.0.

20. The process of claim 18 wherein the antibacterial liquid solution is supplied via a positive displacement pump operatively communicated to an end of the fiber.

* * * * *